(12) United States Patent
Pathak et al.

(10) Patent No.: US 6,596,471 B2
(45) Date of Patent: Jul. 22, 2003

(54) METHOD OF CROSS-LINKING TISSUE WITH A BIS-MALEIMIDE COMPOUND

(75) Inventors: Chandrashekhar P. Pathak, Austin, TX (US); Mark A. Moore, Austin, TX (US); Richard E. Phillips, Jr., San Marcos, TX (US)

(73) Assignee: Carbomedics Inc., Austin, TX (US)

( * ) Notice: Subject to any disclaimer, the term of this patent is extended or adjusted under 35 U.S.C. 154(b) by 0 days.

(21) Appl. No.: 09/747,023

(22) Filed: Dec. 21, 2000

(65) Prior Publication Data

US 2002/0119563 A1 Aug. 29, 2002

(51) Int. Cl.[7] .................. G01N 1/30; G01N 33/48; A61F 2/02; C12B 1/02; A01N 1/02
(52) U.S. Cl. ............ 435/1.1; 435/40.52; 435/29; 435/40.5; 424/423
(58) Field of Search ................ 424/423; 435/29, 435/40.5, 40.52, 1.1

(56) References Cited

U.S. PATENT DOCUMENTS 5,583,114 A * 12/1996 Barrows et al. ............ 514/21
6,132,986 A * 10/2000 Pathak et al. ............ 435/40.5
6,258,870 B1 * 7/2001 Hubbell et al. ............ 522/26

OTHER PUBLICATIONS

Cheronis et al. J. Med. Chem. (1992), 35 (9), 1563–1572.*

* cited by examiner

*Primary Examiner*—Sandra E. Saucier
*Assistant Examiner*—Vera Afremova
(74) *Attorney, Agent, or Firm*—Timothy L. Scott; Williams, Morgan & Amerson, P.C.

(57) ABSTRACT

Herein is disclosed a method of cross-linking a tissue, comprising treating the tissue under effective cross-linking conditions with a diunsaturated organic compound comprising structure I:

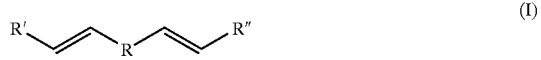

(I)

wherein R, R', and R" are each independently an organic moiety having from 1 to 20 carbon atoms.

Also disclosed is a cross-linked biological tissue produced by treating the tissue according to the above method.

13 Claims, No Drawings

METHOD OF CROSS-LINKING TISSUE WITH A BIS-MALEIMIDE COMPOUND

BACKGROUND OF THE INVENTION

1. Field of the Invention

The present invention relates generally to the field of preparing tissue for prosthetic use. More particularly, it concerns methods of crosslinking tissues with diunsaturated organic compounds.

2. Description of Related Art

Bioprostheses are devices derived from processed biological tissues to be used for implantation into a mammalian (e.g., human) host. Implantation of bioprostheses is a rapidly growing therapeutic field as a result of improvements in surgical procedures and immunosuppressive treatments, as well as increased knowledge of the graft-host interaction.

Several applications for tissue transplantation are known. For example, heart malfunction due to heart valve disorders can often be treated by surgically implanting a prosthetic valve. Treated tissue derived from porcine aortic valves or bovine pericardium is often used for this application. Other applications include tendons, ligaments, skin patches, pericardial patches, aortic patches, and tympanic membranes, among others. In the majority of known applications, the primary component of a bioprosthesis is collagen.

Several problems associated with tissue transplantation include inflammation, degradation, calcification, and immune rejection. Attempts have been made to overcome these problems by tissue cross-linking (also referred to as "tissue fixation"). Cross-linking involves the use of bi- or multifunctional molecules having reactive groups capable of forming stable intra- and intermolecular bonds with reactive amino acid side groups present in the bioprosthesis, often on collagen.

Glutaraldehyde is a bifunctional molecule capable of reacting under physiological conditions with the primary amine groups of collagen. Although it is the most commonly used chemical fixative for biological tissues, glutaraldehyde has a number of drawbacks associated with its use in cross-linking tissues for bioprosthetic use. For example, the long term durability of glutaraldehyde-fixed bioprostheses is not well established, particularly in view of a number of reports of mechanical failures of the tissue at points of high mechanical stress (Broom, 1977; Magilligan, 1988). Another drawback to glutaraldehyde fixation of bioprostheses is depolymerization of the cross-links in vivo, resulting in release of toxic glutaraldehyde into the host (Moczar et al., 1994; Wiebe et al., 1988; Gendler et al., 1984).

Further shortcomings of glutaraldehyde-cross-linking are related to the chemistry of the molecule. Glutaraldehyde forms a relatively unstable Schiff-base bond with collagen. In water, such as an aqueous solution of glutaraldehyde prior to performing a cross-linking treatment, glutaraldehyde can polymerize to form a water-soluble polyether polymer.

In addition, glutaraldehyde-cross-linked bioprostheses have an undesirable propensity to calcify after implantation. This calcification is widely held to be the predominant cause of failure of glutaraldehyde-cross-linked devices (Golomb et al., 1987; Levy et al., 1986; Thubrikar et al., 1983; Girardot et al., 1995). Increased calcium uptake by a bioprosthesis typically leads to an accumulation of calcium phosphate, which in turn mineralizes into calcium hydroxyapatite. The calcification process is not well understood, but appears to depend on factors such as calcium metabolism diseases, age, diet, degeneration of tissue components such as collagen, and turbulence. Calcification of bioprostheses has been associated with degenerative changes in glutaraldehyde-treated collagen fibers.

A number of approaches have been investigated for reducing calcification of glutaraldehyde-fixed bioprostheses. For example, glutaraldehyde-fixed bioprosthetic heart valves have been treated with surfactants to reduce calcification after implantation (U.S. Pat. No. 5,215,541). In another approach, alpha-aminooleic acid treatment of glutaraldehyde-fixed tissue has been reported as an effective biocompatible, non-thrombogenic approach for minimizing calcification of bioprostheses (Girardot et al., 1991; Gott et al., 1992; Girardot et al., 1993; Hall et al., 1993; Myers et al., 1993; Girardot et al., 1994). The broad applicability of this approach in the production of bioprostheses, however, may be limited by the inability to achieve good tissue penetration by alpha-aminooleic acid into glutaraldehyde-fixed tissue (Girardot, 1994).

With respect to the biocompatibility of prosthetic devices, implantation of bioprostheses in living tissues typically initiates a series of physiological events which can activate host defense mechanisms such as coagulation, platelet adhesion and aggregation, white cell adhesion, and complement activation, among others. In attempts to improve the biocompatibility or hemocompatibility of articles adapted for use in contact with blood or blood products, aliphatic extensions have been added to the surface of bioprostheses in order to provide hydrophobic binding sites for albumin. The binding of albumin to a bioprosthesis has been reported to provide a low activation of coagulation, low complement activation, and reduced platelet and white cell adhesion, thereby providing improved hemocompatibility (U.S. Pat. Nos. 5,098,960 and 5,263,992; Munro et al., 1981; Eberhart, 1989).

Some cross-linking agents have been investigated as alternatives to glutaraldehyde. These include polyepoxides, diisocyanates, di- and polycarboxylic acids, and photooxidation using organic dyes (see Khor, 1997, for review).

Therefore, a need exists within the field of bioprosthetics for simple, cost-effective methods for cross-linking biological tissues which provide bioprostheses with more desirable mechanical characteristics, reduced susceptibility to calcification, or enhanced biocompatibility relative to bioprostheses produced from glutaraldehyde-cross-linked tissue.

It is well known that a thiol may undergo addition to an unsaturated organic compound to form a thioether.

SUMMARY OF THE INVENTION

In one embodiment, the present invention relates to a method of cross-linking a tissue, comprising treating the tissue under effective cross-linking conditions with a diunsaturated organic compound. Preferably, the diunsaturated organic compound is a solute in a fluid comprising a solvent.

In another embodiment, the present invention relates to a cross-linked biological tissue produced by treating the tissue under effective cross-linking conditions with a diunsaturated organic compound. Preferably, the diunsaturated organic compound is a solute in a fluid comprising a solvent.

The method allows cross-linking of tissues to an extent comparable to that seen for glutaraldehyde cross-linking.

DESCRIPTION OF ILLUSTRATIVE EMBODIMENTS

In one embodiment, the present invention relates to a method of cross-linking a tissue, comprising treating the tissue under effective cross-linking conditions with a diunsaturated organic compound.

The tissue to be treated can be any tissue from which it is desired to fashion a bioprosthesis. A variety of tissues can be used, such as tendons, ligaments, heart valves, tissues usable to construct heart valves such as dura mater and pericardium, skin patches, pericardial patches, aortic patches, and tympanic membranes, among others. The tissue to be treated can be derived from any of a variety of animal species, such as humans, cattle, pigs, horses, sheep, rabbits, rats, ostriches, or kangaroos, among others.

By "diunsaturated organic compound" is meant any compound comprising structure I:

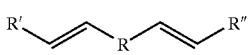

(I)

wherein R, R', and R'' are each independently an organic moiety having at least 1 carbon atom. Exemplary organic moieties include alkanes, substituted alkanes, alkenes, substituted alkenes, or oligomers of any of the foregoing, among others. The organic moieties can be linear, branched, cyclic, or polycyclic, among others, and R can independently form a cyclic or polycyclic moiety with R', R'', or both. If the organic moiety is substituted, exemplary substituents include hydroxy, carboxy, and keto groups; maleimide groups; and halides, among others.

In one preferred embodiment, the diunsaturated organic compound is a bis-maleimide compound with structure II:

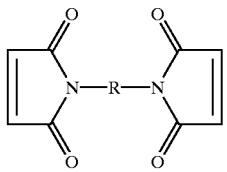

(II)

wherein R is an organic moiety comprising at least 1 carbon atom.

In one preferred embodiment, R is a polyalkyleneoxide group comprising at least 1 repeat unit. More preferably, R is a polyethyleneoxide, a polypropyleneoxide, or a polybutyleneoxide, and R comprises at least 3 repeat units. In another preferred embodiment, R has the structure —(CH$_2$)$_6$— (i.e., the diunsaturated organic compound is 1,6-bis-maleimidohexane).

The term "diunsaturated organic compound" also includes compounds having more than two >C=C< groups, i.e. compounds wherein one or more of R, R', or R'' comprises at least one >C=C< group.

Preferably, the diunsaturated organic compound is a solute in a fluid comprising a solvent. The fluid comprising the diunsaturated organic compound also comprises a solvent. The solvent can be any liquid in which the compound is soluble and in which the compound does not undergo degradation or side reactions. Typically, if R, R', or R'' is an unsubstituted hydrocarbon, the diunsaturated organic compound is not soluble in water but is soluble in organic solvents, such as dimethyl sulfoxide (DMSO). Preferably, the organic solvent is soluble in water, and thus is able to readily penetrate tissues. If R, R', and R'' are substituted hydrocarbons or oligomers of substituted hydrocarbon, such as oligomers of ethylene oxide, the diunsaturated organic compound is typically soluble in water.

The concentration of the diunsaturated organic compound in the fluid is preferably between about 0.1 mg/mL and about 100 mg/mL. More preferably, the concentration is between about 1 mg/mL and about 20 mg/mL.

The fluid can also comprise other additives that do not interfere with the cross-linking properties or other desirable properties of the fluid. Such additives include preservatives and adjuvants, among others.

The compound, as well as any other additives, can be synthesized by any known technique. Alternatively, the compound may be commercially available (e.g., 1,8-bis-maleimidotriethylene glycol and 1,6-bis-maleimidohexane are commercially available from Pierce, Rockford, Ill.). The fluid can be prepared, typically, by dissolution of the compound, and any other additives, in the solvent. After preparation of the fluid, the fluid can be stored at any temperature and pH desired. The temperature and pH of storage need not be those which are effective for cross-linking. If necessary, prior to use, the pH and the temperature can be adjusted to the preferred ranges described below by known techniques.

The pH of the fluid can be any pH which is not deleterious to the tissue being treated or the cross-linking reaction. The pH of the fluid can be adjusted by any appropriate technique. Typically, the pH of the fluid is between about pH 6 and about pH 10. This pH range allows cross-linking to be relatively rapid and have a relatively low amount of side-reactions. Preferably, the pH of the fluid is between about pH 6.5 and about pH 8. More preferably, the pH of the fluid is between about pH 6.8 and about pH 7.5.

The temperature of the fluid can be any temperature at which the cross-linking reaction is relatively rapid and a relatively low amount of side reactions occur. Preferably, the temperature of the fluid is between about 0° C. and about 60° C. More preferably, the fluid temperature is between about 2° C. and about 30° C. Conveniently, the reaction may be carried out at room temperature (20–25° C.).

One of ordinary skill in the art will recognize that the duration of treatment is not critical, so long as the tissue and the diunsaturated organic compound remain in contact long enough to cross-linking to proceed to a sufficiently great extent. The duration of treatment may vary depending on the tissue being treated or the diunsaturated organic compound being used for cross-linking. Typically, treatment duration is in the range of from about 1 min to about 24 hr. Preferably, treatment duration is at least about 30 min, more preferably at least about 6 hr.

The extent of cross-linking can be modified by varying any of several parameters, such as the diunsaturated organic compound used for cross-linking, possible pretreatment of the tissue with an agent that effects the cross-linking properties of the diunsaturated organic compound, the duration of treatment, the pH of treatment, the temperature of treatment, and other parameters apparent to one of ordinary skill in the art. The extent of cross-linking desired from a given performance of the method will depend on the physical properties and biocompatibility desired for a prosthesis made from the cross-linked tissue, among other properties apparent to one of ordinary skill in the art.

Though not to be bound by theory, it is believed that, when a diunsaturated organic compound is used to crosslink a tissue, the thiols present in the side chains of cysteine residues found in collagen or other proteins present in the tissue form thioether linkages with the unsaturated moieties of the diunsaturated organic compound. Other side reactions may occur.

The typical concentration of cysteine in bovine pericardial tissue is about 8 residues per 1000 residues. This is comparable to the typical concentration of histidine in bovine pericardial tissue (roughly 6–10 residues per 1000 residues), which amino acid residue is known to be consumed in photooxidative crosslinking.

The result of the cross-linking reaction is a cross-linked tissue. Preferably, at least about 50 mol % of the thiol groups of the cross-linked tissue are components of thioether bonds between the tissue and the crosslinking agent. Preferably, the cross-linked tissue has a shrink onset temperature at least about 3° C. greater than that of the tissue without crosslinking. Regardless of the mole fraction of thiol groups consumed in crosslinking, the cross-linked tissue is suitable for use in a bioprosthesis. The cross-linked tissue can be formed into a bioprosthesis or a component of a bioprosthesis following techniques that are known in the art. After the bioprosthesis is formed from the tissue, it can be implanted into an animal, preferably a mammal, following techniques known in the art.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Cross Linking of Bovine Pericardium

Materials and Methods: Bovine pericardium was obtained from an abattoir and cleaned according to methods known in the art of bioprosthesis manufacturing. Unfixed bovine pericardium tissue was obtained from the tissue manufacturing department of Sulzer Carbomedics and was stored in a high salt/high sugar preservative solution (HSHS) before being rinsed for approximately 1 hr in phosphate-buffered saline (PBS) prior to use. Photooxidized bovine pericardium tissue (positive control 1) was supplied by the tissue manufacturing department of Sulzer Carbomedics. Glutaraldehyde-fixed bovine pericardium tissue (positive control 2) was obtained by fixing bovine pericardium in 0.25% glutaraldehyde for a minimum of 2 wks.

Tissue Crosslinking: 10 mg 1,8-bis-maleimidotriethylene glycol (BM(PEO)) (Pierce, Rockford, Ill., Lot #AJ41572) was dissolved in 100 µL dimethyl sulfoxide (DMSO) and brought to 1 mL by the addition of 900 µL PBS. Two 1 cm² unfixed HSHS-stored bovine pericardium tissue pieces were placed in the BM(PEO) solution overnight (~20 hr) at room temperature. After overnight treatment, samples were rinsed in ultrafiltered water for ~30 min, and then stored in 40% isopropanol/HEPES solution.

Similarly, 1,6-bis-maleimidohexane (BMH) (Pierce, Lot #99030863) was used to fix HSHS-stored bovine pericardium.

Two 1 cm² bovine pericardium pieces treated with DMSO alone provided a negative control.

Protein Extraction Assay: Some crosslinked samples underwent protein extraction assays using a standard procedure established at Sulzer Carbomedics. To summarize, 10–20 mg of tissue was extracted with a 10–20 µL extraction solution containing 50 mM Tris-HCl (pH 6.8), 10% glycerol, 4% mercaptoethanol, 1% sodium dodecyl sulfate (SDS), 0.5 M NaCl, and 0.01% bromophenol blue. The extracted solution was then run on a 4–20% acrylamide:bisacrylamide (37.5:1 Mini-PROTEAN II) Gradient Ready Gel (Biorad, Richmond, Calif.) and the gel underwent densitometry. QuantiScan for Windows (densitometer program) was used to calculate peak areas of the protein bands on the gel. The QuantiScan peak area for control HSHS tissue and DMSO treated tissue (not shown) showed high extractables, indicating no crosslinking. Therefore, resistance to extraction was calculated as follows:

Resistance to Extraction=100–(QuantiScan peak area under treated tissue/QuantiScan peak area under HSHS or DMSO control*100)

Shrinkage Temperature Assay: The shrinkage temperature of some crosslinked samples was determined using standard differential scanning calorimetric analysis. Briefly, 2–10 mg of tissue was heated at 10° C. increments under nitrogen. Typically, an endotherm is seen in the range of 60° C.–90° C., and this endotherm is attributed to a shrinkage transition.

TABLE 1

Summary of Tissue Crosslinking Treatments

| Sample Code | Tissue Treatment |
| --- | --- |
| HSHS | No treatment; fresh tissue stored in HSHS |
| PO | Standard photooxidation treatment |
| Glut | Fixation by 0.25% glutaraldehyde in PBS |
| BMH | Fixation by 1,6-bis-maleimidohexane (as described above) |
| BM(PEO) | Fixation by 1,8-bis-maleimidotriethylene glycol (as described above) |
| DMSO | Treatment with dimethyl sulfoxide |

Results: The resistance to extraction and shrink onset temperature for the samples are given in Table 2.

TABLE 2

Resistance to extraction and shrink onset temperature

| Sample Code | Resistance to Extraction | Shrink Onset Temperature (° C.) |
| --- | --- | --- |
| HSHS | 0.0 | 66.1 ± 0.4 |
| PO | 79.2 | 66.9 ± 0.4 |
| Glut | 100.0 | 87.0 ± 0.4 |
| BMH | 62.9 | 66.6 ± 0.1 |
| BM(PEO) | 89.7 | 69.5 ± 0.3 |
| DMSO | 0.0 | 66.0 ± 1.6 |

Conclusions: Glutaraldehyde-treated tissue exhibited no extractables and elevated shrink onset temperature relative to the controls, indicating a high degree of crosslinking. The photooxidized control tissue also showed reduced extractables relative to the controls, indicating crosslinking.

Both the BMH-treated and the BM(PEO)-treated tissues exhibited reductions in the level of extractables, and BM(PEO)-treated tissue showed an elevated shrink onset temperature. These results indicate crosslinking occurred. It is believed the poorer resistance to extraction observed for the BMH-treated tissue resulted from poor solubility of BMH in the DMSO/aqueous medium.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

Broom, *J Biomech.* 10:707 (1977)
Eberhart, *IEEE Eng. in Med. and Bio.* 26 (June 1989)
Ellis et al., *Inorg. Chem.*, 31:3026 (1992)
Frautschi, U.S. Pat. No. 5,098,960
Gendler et al., *J. Biomed. Mater. Res.* 18:727 (1984)
Girardot et al., *Trans. Soc. Biomat.* 14:114 (1991)
Girardot et al., *Trans. Soc. Biomat.* 16:266 (1993)
Girardot et al., *Int. J Artif Org.* 17:76 (1994)
Girardot et al., *J. Biomed. Mater. Res.* 29:793 (1995)
Girardot, J. M., et al. *J. Heart Valve Dis.* 5:518 (1996)
Golomb et al., *Am. J Pathol.* 127:122 (1987)
Gott et al., *Ann. Thorac. Surg.* 53:207 (1992)
Guire, U.S. Pat. No. 5,263,992
Hall et al., *ASAIO Proc.* 24 (1993)
Khor, E., *Biomaterials* 18:95 (1997)
Levy et al., in: Williams, D. F., Ed. CRC Critical Rev. in Biocompatibility, Vol. 2. 147 (1986)
Magilligan, *Trans. Am. Soc. Artif Intern. Organs* 34:1031 (1988)
Moczar et al., *ASAIO J* 40:M697 (1994)
Moore, M. A., et al. *Ann. Thorac. Surg* 66:S245 (1998)
Munro et al., *Trans. Am. Soc. Artif Intern. Organs* 27:499 (1981)
Myers et al., *Int. J. Artif Org.* 16:453 (1993)
Nashef et al., U.S. Pat. No. 5,215,541
Sung, H. W., *J. Biomed. Mater. Res.* 42:560 (1998)
Thubrikar et al., *J Thorac. Cardiovasc. Surg* 86:115 (1983)
Wiebe et al., *Surgery* 104:26 (1988)
Zeeman, R., et al. *J. Biomed. Mater. Res.* 46:424 (1999)

What is claimed is:

1. A method of cross-linking a biological tissue, comprising:
   treating the biological tissue under effective cross-linking conditions with a bis-maleimide compound having the structure:

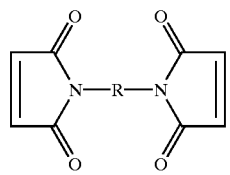

wherein R is —$(CH_2)_6$—, to yield a cross-linked biological tissue.

2. The method of claim 1, wherein the biological tissue is derived from an animal selected from the group consisting of humans, cattle, pigs, horses, sheep, rats, rabbits, ostriches, and kangaroos.

3. The method of claim 1, wherein the biological tissue is selected from the group consisting of tendon, ligament, heart valve, dura mater, pericardium, skin patch, pericardial patch, aortic patch, and tympanic membrane.

4. The method of claim 1, wherein the bis-maleimide compound is provided as a solute in a fluid comprising a solvent.

5. The method of claim 4, wherein the solvent is dimethyl sulfoxide.

6. The method of claim 4, wherein the solvent is water.

7. The method of claim 4, wherein the fluid has a pH between about pH 6 and about pH 10.

8. The method of claim 7, wherein the fluid has a pH between about pH 6.5 and about pH 8.

9. The method of claim 8, wherein the fluid has a pH between about pH 6.8 and about pH 7.5.

10. The method of claim 4, wherein the fluid has a temperature between about 0° C. and about 60° C.

11. The method of claim 10, wherein the fluid has a temperature between about 2° C. and about 30° C.

12. The method of claim 1, wherein the treating is performed for at least about 30 min.

13. The method of claim 12, wherein the treating is performed for at least about 6 hr.

* * * * *